United States Patent [19]

Hacker

[11] Patent Number: Plant 6,724

[45] Date of Patent: Apr. 4, 1989

[54] HACKER'S AUGUST GOLD APPLE TREE

[76] Inventor: Theodore R. Hacker, 956 Stonewall Rd., Lexington, Ky. 40501

[21] Appl. No.: 124,271

[22] Filed: Nov. 23, 1989

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—King and Schickli

[57] ABSTRACT

An apple tree bearing golden-yellow fruit in August.

3 Drawing Sheets

BACKGROUND AND GENERAL STATEMENT OF THE INVENTION

I discovered my new and distinct variety of apple tree, identified by the varietal name Hacker's August Gold, in an old orchard on my cultivated farm located in Fayette County, Lexington, Ky. I noticed that the tree, which apparently grew from a seed or water sprout, bore fruit having a green-silver tint that began ripening to a golden-yellow during the month of August. This ripening occurs several weeks prior to the known Golden Delicious varieties of apple tree.

The tree and fruit were carefully preserved and protected. During the course of the following five years, the same characteristics were observed without any significant variation.

Since the initial discovery, several second generation trees have been grown from grafts of the original tree. I have observed that the characteristics described above persist already through the second generation. The original tree and its descendents have the very same characteristics and fruit color.

DESCRIPTION OF THE DRAWINGS

The accompanying photographic drawings illustrate the new variety of apple tree and the characteristics of its fruit.

DESCRIPTION OF THE NEW VARIETY

Figure 1:
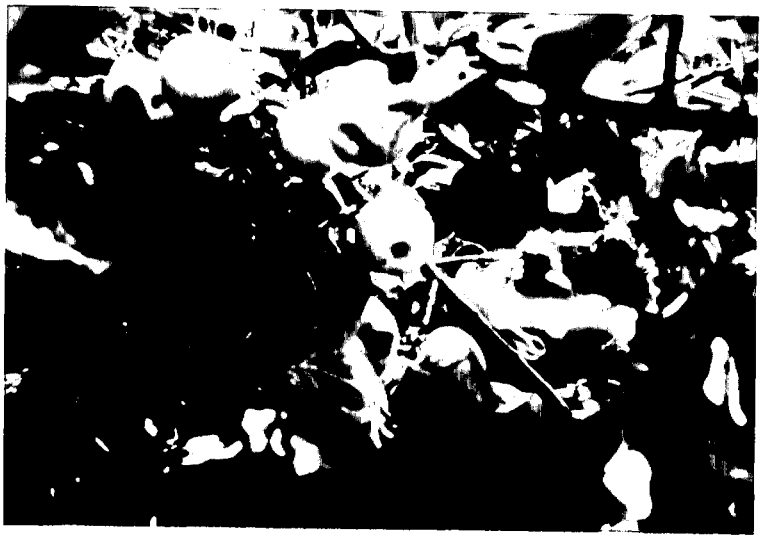
FIGS. 1-3 are photographs showing the parent Hacker's August Gold apple tree in its fruit bearing condition illustrating its fruit during the 1st week of August, 1987.
Figure 2:
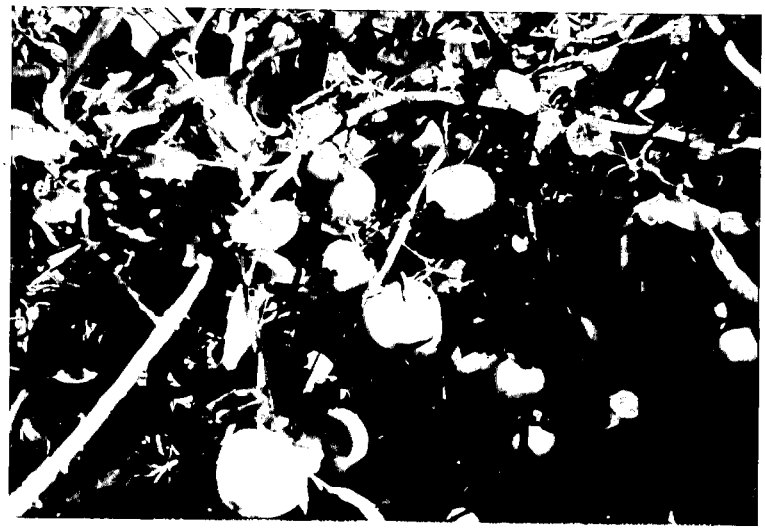
Figure 3:
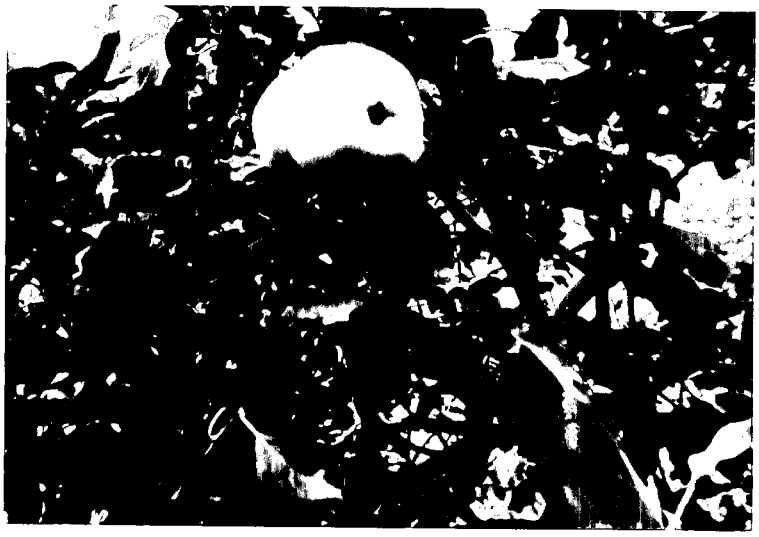
Figure 4:
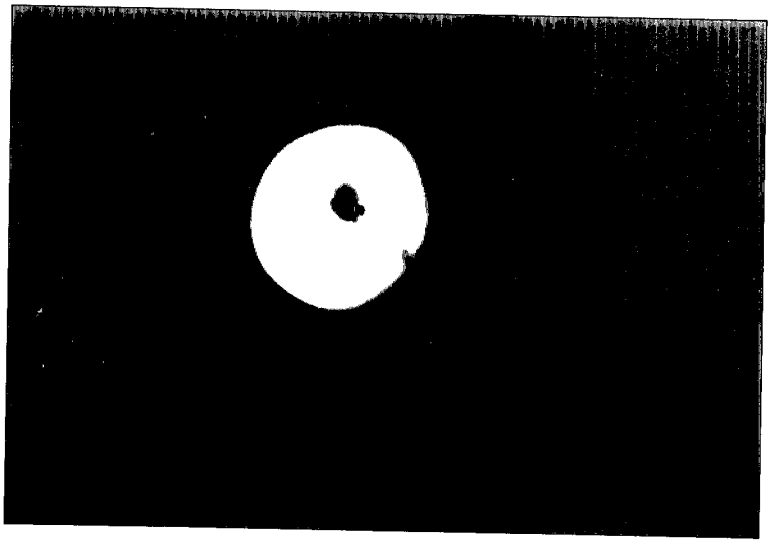
FIGS. 4-6 are photographs of the top, bottom and side respectively of one apple of mature fruit showing the shape and coloring.
Figure 5:
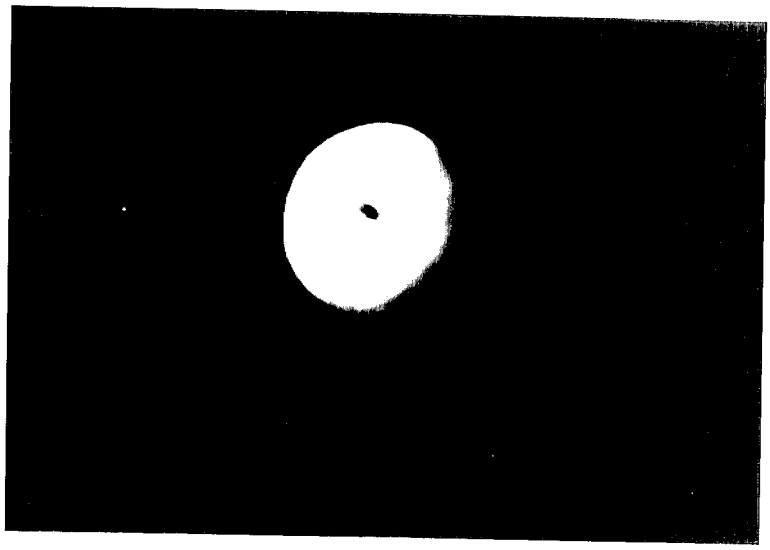
Figure 6:
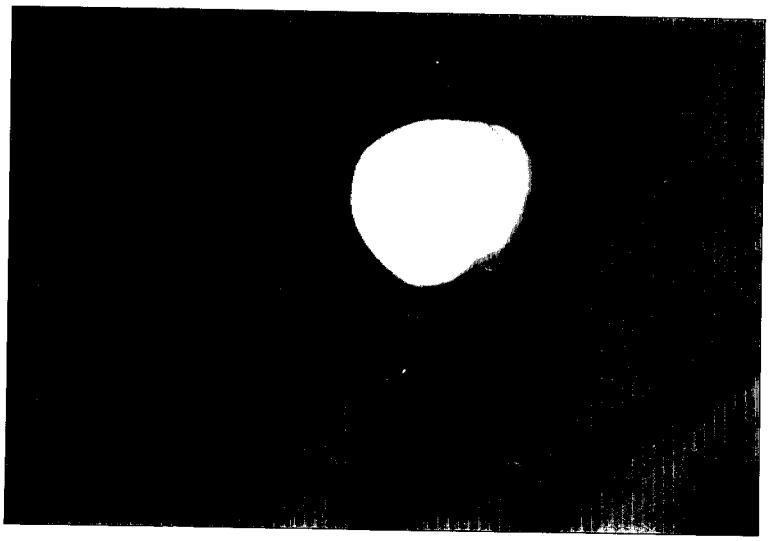
Figure 7:
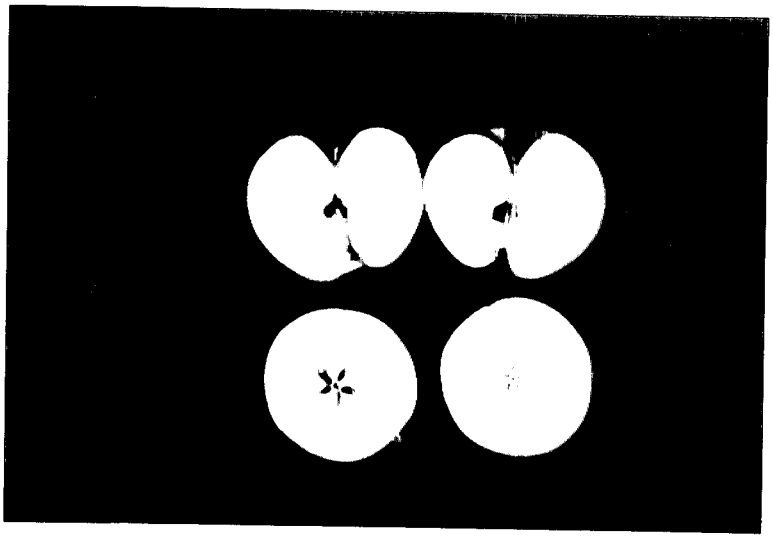
FIG. 7 shows two apples of mature fruit, one cut in half along the stem line and one cut in half perpendicular to the stem line.

This new variety exhibits all the extremely favorable qualities with respect to production, storage and consumption for which the Golden Delicious varieties are known. As an additional characteristic, however, this new variety shows as a major feature, a maturity of several weeks (approximately 3-6) earlier in the season than the known Golden Delicious varieties.

The specimens described were grown in Fayette County, Ky. The color descriptions that follow refer to "Dictionary of Color", Maery and Paul, Second Editions.

Tree: Small to medium, reaching 20'-25' in height; medium grower, hardy, very productive, regular bearer; oval shape with many central limbs providing a dense appearance.

Trunk: Medium to small for tree this size; brown bark; twisted appearance.

Branches: Much branching; medium thickness; smooth, relatively few lenticels; medium size lenticels.

Leaves: Length 2-3¼"; width, 1½ to 2¼"; color medium green (top face: Plate 23, J6; bottom face: Plate 21, J1 — "Dictionary of Color"); shape oblong to oval; color of veins on back of leaves, light to yellow green (Plate 21, B1 — "Dictionary of Color"); leaves have 6-7 mid-ribs and alternate on stem.

Flowers: Time of flowering, 5-7 days later than known Golden Delicious varieties in Lexington, Ky.; small to medium in size; white in color; cream colored pedicels; yellow to cream colored stamens; green sepals.

Fruit:

*Date of first and last picking.*—Approximately July 25-August 20.

*Size and shape.*—Average of vertical diameter 2½" and average horizontal diameter up to 3½".

*Stem.*—Relatively short and thick.

*Stem cavity.*—Relatively wide and conical.

*Skin.*—Thin with very smooth texture; immature fruit light green with silvery tint; mature fruit golden in color (Plate 10, H1 — "Dictionary of Color").

*Core and seeds.*—Five seed cavities with 1-5 seeds.

*Flesh.*—White with firm bits of spicy, sweet juice; tender, fine cell structure; excellent quality.

*Basin.*—More like McIntosh than Delicious varieties; shape is a flat to oval resembling McIntosh; generally five crowns; depth of basin approximately ⅛".

*Time of maturity relative to Golden Delicious.*—About one month earlier.

Use: Dessert, culinary, juice, sauce.

I claim:

1. A new and distinct variety of fruiting apple tree named Hacker's August Gold and parts thereof as described and illustrated, characterized by its silvery green fruit which ripens to a golden yellow.

* * * * *